US00PP27472P2

(12) United States Plant Patent
Oprins

(10) Patent No.: US PP27,472 P2
(45) Date of Patent: Dec. 20, 2016

(54) *HYDRANGEA* PLANT NAMED 'HPOPR013'

(50) Latin Name: *Hydrangea paniculata*
Varietal Denomination: Hpopr013

(71) Applicant: Jan Oprins, Rijkevorsel (BE)

(72) Inventor: Jan Oprins, Rijkevorsel (BE)

(73) Assignee: OPRINS PLANTS, N.V., Rijkevorsel (BE)

( * ) Notice: Subject to any disclaimer, the term of this patent is extended or adjusted under 35 U.S.C. 154(b) by 257 days.

(21) Appl. No.: 13/987,927

(22) Filed: Sep. 16, 2013

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS http://hortensjebabopielki.blogspot.com/2013/03/hydrangea-paniculata-hortensja_23.html; Mar. 23, 2013; 7 pages.*

* cited by examiner

*Primary Examiner* — Kent L Bell
(74) *Attorney, Agent, or Firm* — Penny J. Aguirre

(57) ABSTRACT

A new cultivar of *Hydrangea paniculata* named 'Hpopr013', that is characterized by its conical shaped inflorescences with pointed apices, its gray-purple stems, its sterile flowers that open yellow-green and fade to pink, and its upright plant habit.

2 Drawing Sheets

Genus/species: *Hydrangea paniculata.*
Varietal denomination: 'Hpopr013'.

BACKGROUND OF THE INVENTION

The present invention relates to a new and distinct cultivar of *Hydrangea paniculata* and will be referred to hereafter by its cultivar name, 'Hpopr013'. 'Hpopr013' represents a new lacecap type *Hydrangea*, a deciduous shrub grown for landscape use and for use as a potted plant.

The new cultivar of *Hydrangea*, 'Hpopr013, was discovered by the Inventor as a chance seedling in a trial garden in Rijkevorsel, Belgium in June 2010. The exact parentage is unknown, however 'Dharuma' (not patented) and 'Pink Diamond' (not patented) are thought to be probable parents based on the characteristics of the new cultivar and their proximity to the new cultivar.

Asexual propagation of the new cultivar was first accomplished by the Inventor by softwood cuttings in June of 2010 in Rijkevorsel, Belgium. Asexual propagation by softwood cuttings and tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish in 'Hpopr013' as a unique cultivar of *Hydrangea.*

1. 'Hpopr013' exhibits conical shaped inflorescences with pointed apices.
2. 'Hpopr013' exhibits gray-purple stems.
3. 'Hpopr013' exhibits sterile flowers that open yellow-green and fade to pink.
4. 'Hpopr013' exhibits an upright plant habit.

'Dharuma', a probable parent of 'Hpopr013', differs from 'Hpopr013' in having cylindrical inflorescences with an obtuse top and in having a less upright growing habit. 'Pink Diamond, a probable parent of 'Hpopr013', differs from 'Hpopr013' in having broader and less pointed inflorescences and white sterile flowers that fade to soft pink. 'Hpopr013' can be most closely be compared to *Hydrangea paniculata* cultivars 'Limelight' (U.S. Plant Pat. No. 12,874) and 'DVPpinky' (U.S. Plant Patent No. 16,166). 'Limelight' is similar to 'Hpopr013' in having yellow-green mature sterile flowers. 'Limelight' differs from 'Hpopr013' in having broader inflorescences with obtuse apices, in having sterile flowers that fade to a lighter pink color, and in having fewer fertile flowers. 'DVPpinky' is similar to 'Hpopr013' in having conical shaped inflorescences. 'DVPpinky' differs from 'Hpopr013' in having sterile flowers that fade to a dark pinkish red to purple-red color and in having fewer fertile flowers.

BRIEF DESCRIPTION OF THE DRAWINGS

The accompanying colored photographs illustrates the overall appearance and distinct characteristics of a four year-old plant of the 'Hpopr013', as grown outdoors in a field in Stroe, The Netherlands. The plant was placed in a container for photographs.

The photograph in FIG. 1 provides a side view of a plant of 'Hpopr013'.

Figure 1:
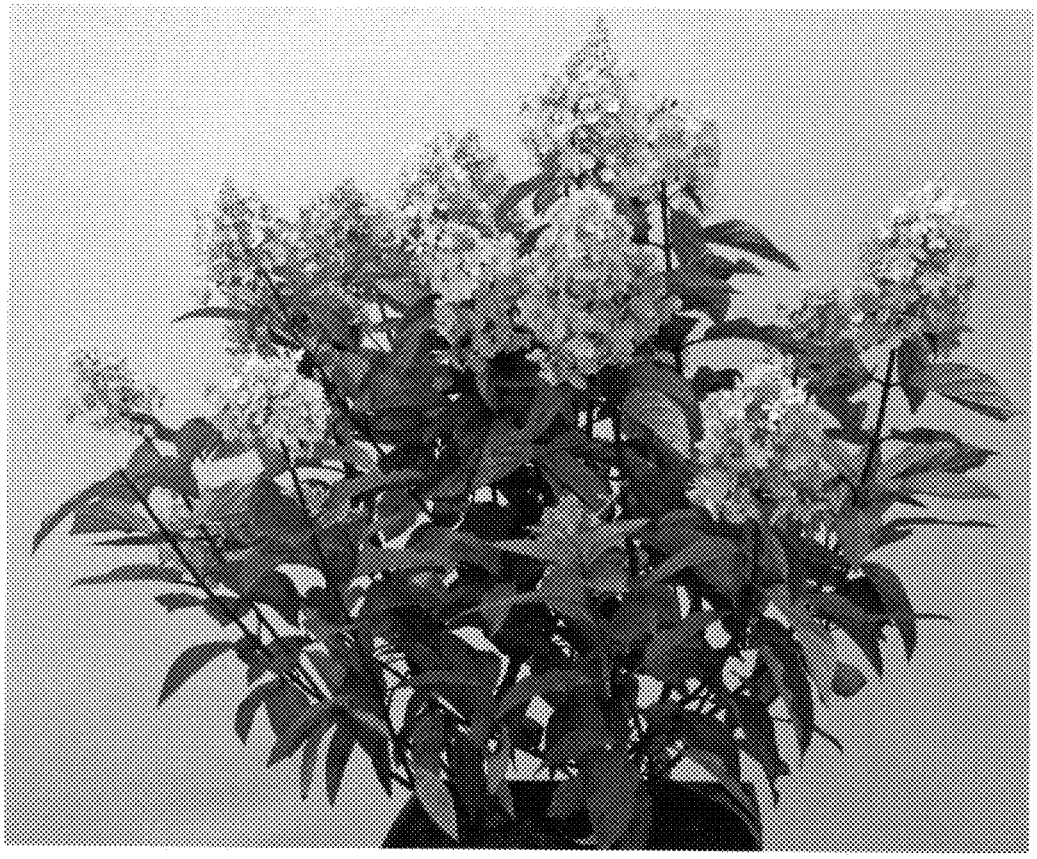
Figure 2:
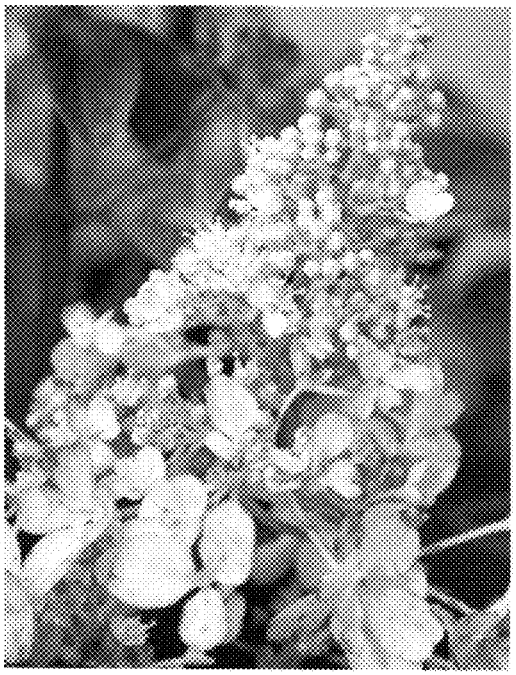

The photograph in FIG. 2 provides a close-up view of a maturing inflorescence of 'Hpopr013'.

Figure 3:
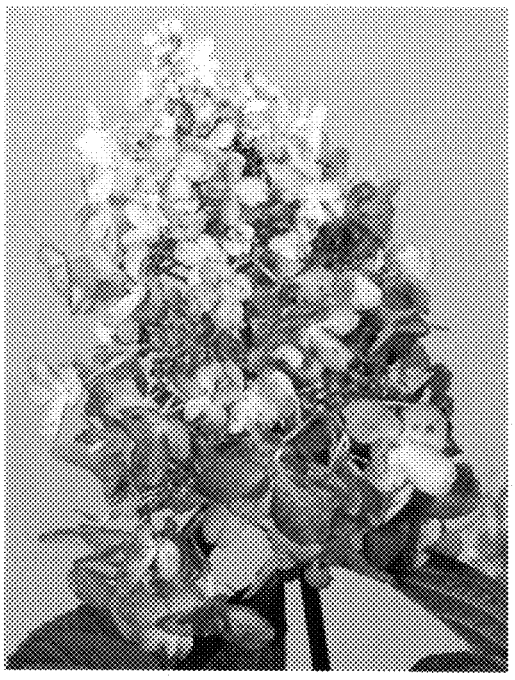

The photograph in FIG. 3 provides a close-up view of a mature inflorescence of 'Hpopr013'.

Figure 4:
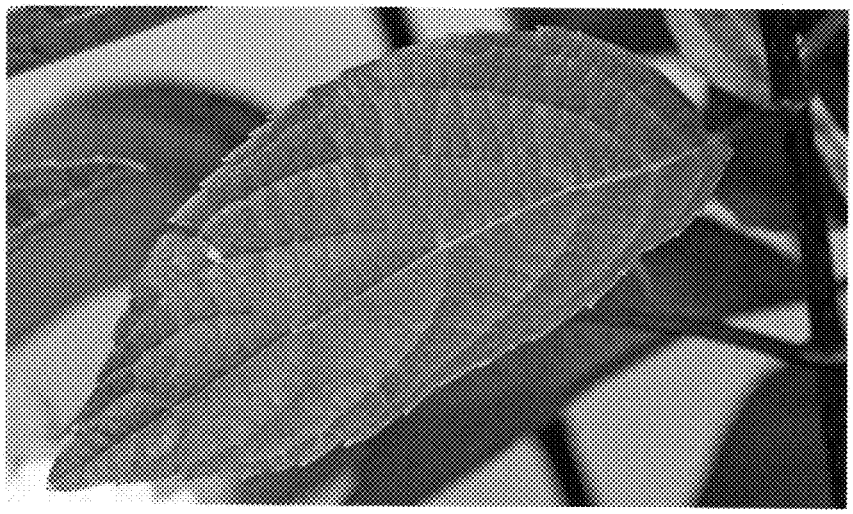

The photograph in FIG. 4 provides a close-up view of a leaf of 'Hpopr013'.

The colors in the photographs may differ slightly from the color values cited in the detailed botanical description, which accurately describe the colors of the new *Hydrangea*.

BOTANICAL DESCRIPTION OF THE PLANT

The following is a detailed description of the new cultivar as observed on 4 year-old plants as grown outdoors in Stroe, the Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Approximately 8 weeks from June to August in Stroe, The Netherlands.

*Plant habit.*—Broad upright.

*Height and spread.*—Reaches 2.5 m in height and spread.

*Hardiness.*—At least in U.S.D.A. Zones 4 to 9.

*Diseases and pests.*—Similar susceptibility or resistance to diseases or pests as other *Hydrangea* varieties.

*Root description.*—Fibrous and fine roots.

*Propagation.*—Softwood cuttings (preferred) or tissue culture.

*Growth rate.*—Moderately vigorous.

Stem description:

*Shape shape.*—Rounded.

*Stem color.*—New wood; 148C to 148D, sunny side 184C, mature wood; 165A to 200C, lenticels; 165B.

*Stem size.*—Average of 42.6 cm in length and 5 mm in diameter.

*Stem surface.*—Glabrous.

*Stem aspect.*—Average angle 45° (soil level=0°).

*Internode length.*—Average of 4.5 cm.

*Branching.*—Basal branches with two branches produced per stem if pinched.

Foliage description:

*Leaf shape.*—Ovate.

*Leaf division.*—Simple.

*Leaf size.*—Average of 11.6 cm in length and 6.1 cm in width.

*Leaf base.*—Rounded to truncate.

*Leaf apex.*—Acute to short apiculate.

*Leaf venation.*—Pinnate, color upper surface; 152C with 187D towards the base, color lower surface; 182B to 182C with 182A towards the base.

*Leaf margins.*—Serrated.

*Leaf attachment.*—Petiolate.

*Leaf arrangement.*—Opposite.

*Leaf surface.*—Both surfaces dull and slightly rugose, upper surface sparsely strigose, lower surface slightly strigose on main vein and secondary veins, strigose hairs are an average length of 0.5 mm and NN155C to NN155D in color.

*Leaf color.*—Newly formed leaves upper surface; 143A to 143B, newly formed leaves lower surface; 144A, mature leaves upper surface; N137B, mature leaves lower surface; 146C to 147B.

*Petioles.*—Average of 2.4 cm in length and 3 mm in diameter, upper surface; 187A to 187B in color, dull and moderately pubescent with hairs an average length of 0.5 mm and 156D in color, lower surface; 182A in color, dull and sparsely pubescent with hairs and average length of 0.3 mm and 156D in color.

Inflorescence description:

*Inflorescence type.*—Terminal panicle, lacecap in form comprised of a center region of fertile flowers surrounded by an outer ring of single sterile flowers.

*Lastingness of inflorescence.*—Persistent with color lasting from summer to early autumn.

*Inflorescence number.*—One per lateral or sublateral stem.

*Inflorescence size.*—Average of 18.2 cm in depth and 13.8 cm in diameter.

*Flower number.*—Average of 200 sterile flowers and 375 fertile flowers per panicle.

*Flower fragrance.*—None.

*Flower aspect.*—Sterile flowers; outward, more drooping when fading, fertile flowers; upright to outward.

*Flower size.*—Sterile flowers; an average of 3.2 cm in diameter and 9 mm in depth, fertile flowers; an average of 6 mm in diameter and 5 mm in depth.

*Flower type.*—Rotate.

*Flower buds.*—Sterile flowers; average of 6 mm in length and 5 mm in diameter, obovate in shape, 150D tinged with 58A in color, fertile flowers; average of 3 mm in length and 2.5 mm in width, broad obovate in shape, 157B tinged at the top with 68B in color.

*Peduncles.*—Moderately strong, main peduncle (rachis) an average of 18 cm in length and 4 mm in width, 165A to 200C in color, surface glabrous, secondary peduncle an average of 5 cm in length and 1.5 mm in width and 157B in color, surface pubescent.

*Pedicels.*—Sterile flowers; held at an 80° angle from vertical, an average of 2 cm in length and 1 mm in width, moderate strength, 157B in color, dull, moderately pubescent surface covered with adpressed hairs 0.5 mm in length and NN155D in color, fertile flowers; held at all angles, an average of 2 mm in length and 0.5 mm in diameter, moderate strength, dull, glabrous surface, 145B to 145C in color.

*Petals.*—Fertile flowers; average of 5, rotate in arrangement, ovate in shape, entire margin, acute apex, cuneate base, average of 3 mm in length and 1.5 mm in width, upper surface glabrous and moderately glossy, lower surface glabrous and slightly glossy, color; upper surface when opening NN155D, lower surface when opening NN155D suffused with 68B, upper surface when fully opened NN155B, lower surface when fully opened NN155D suffused with 68C, color is not fading, self-cleaning, sterile flowers; average of 4, rotate in arrangement, ovate and concave in shape, an average of 3 cm in length and 1.5 cm width, broadly acute apex, cuneate base, entire margins, glossy and glabrous on upper and lower surface, color upper and lower surface when opening; NN155D, color when mature, upper and lower surface; NN155A, non-fading and non-persistent.

*Sepals.*—Sterile flowers; average of 4, rotate in arrangement, obovate to ovate in shape, an average of 1.9 cm in length and 1.4 cm width, retuse to rounded apex, cuneate base, entire margins, dull and glabrous on upper and lower surface, color upper and lower surface when opening; 155A, color when mature, upper and lower surface; 145C, color fades to a blend of 58A and 185B on both upper and lower surfaces, fertile flowers; average of 5, short triangular in shape, entire margin, broad acute apex, broad cuneate base, average of 1 mm in length and 1.5 mm in width, smooth and slightly glossy on both surfaces, color of upper and lower surface when opening and when fully open 157A, color not fading.

Reproductive organs: (Present on fertile flowers and occasionally on sterile flowers).

*Stamens.*—Sterile flowers; average of 8, anther is double reniform in shape, 0.4 mm in length and 156D in color, filament is 2 mm in length and NN155D in color, pollen is low in quantity and 156C in color, fertile flowers; average of 10, anther is double reniform in shape, 0.4 m in length and 156D in color, filament is 3 mm in length and NN155D in color, pollen is low in quantity and 156C in color.

*Pistils.*—Sterile flowers; average of 2, average of 1 mm in length, stigma is flattened on top of style and 156D in color, style is an average of 0.5 mm in length and 157A in color, ovary is 145D in color, fertile flowers; average of 2, an average of 1 mm in length, stigma is flattened on top of style and 156D in color, style is an average of 0.5 mm in length and 157A in color, ovary is 157A in color.

*Fruit and seed.*—Has not been observed to date.

It is claimed:

1. A new and distinct cultivar of *Hydrangea* plant named 'Hpopr013' as herein illustrated and described.

* * * * *